United States Patent [19]
DeCarlo, Jr. et al.

[11] Patent Number: 6,162,226
[45] Date of Patent: Dec. 19, 2000

[54] LONG BONE REAMER WITH DEPTH STOP INDICATOR

[75] Inventors: Alfred F. DeCarlo, Jr., Stamford, Conn.; Patricia Katzman, Arlington, Mass.

[73] Assignee: DePuy Orthopaedics, Inc., Warsaw, Ind.

[21] Appl. No.: 09/161,035

[22] Filed: Sep. 25, 1998

[51] Int. Cl.$^7$ ........................................ A61B 17/58
[52] U.S. Cl. .......................... 606/80; 606/96; 408/202; 408/203
[58] Field of Search ................. 606/79, 80, 85, 606/86, 96; 408/202, 203, 241 S

[56] References Cited

U.S. PATENT DOCUMENTS

| | | | |
|---|---|---|---|
| 74,466 | 2/1868 | Whiting | 408/202 |
| 294,985 | 3/1884 | Fuller, Sr. | 408/202 |
| 803,939 | 11/1905 | Tiede | 408/202 |
| 4,710,075 | 12/1987 | Davison | 408/202 |
| 4,738,256 | 4/1988 | Freeman et al. | 128/92 VV |
| 4,790,852 | 12/1988 | Noiles | 623/18 |
| 5,312,411 | 5/1994 | Steele et al. | 606/88 |
| 5,342,366 | 8/1994 | Whiteside et al. | 606/86 |
| 5,507,801 | 4/1996 | Gisin et al. | 606/96 |
| 5,514,140 | 5/1996 | Lackey | 606/80 |
| 5,607,431 | 3/1997 | Dudasik et al. | 606/80 |
| 5,989,257 | 11/1999 | Tidwell et al. | 606/79 |
| 5,993,453 | 11/1999 | Bullara et al. | 606/79 |

Primary Examiner—Michael Buiz
Assistant Examiner—Julian W. Woo
Attorney, Agent, or Firm—Nutter, McClennen & Fish, LLP

[57] ABSTRACT

The present invention provides an orthopaedic instrument system and method for reaming a long bone to a predetermined depth. The instrument system includes an elongate reamer having a proximal portion and a bone contacting surface with an integral cutting element. A stop indicating sleeve having an axial bore and a stop indicating element is removably disposed about the reamer. The stop indicating sleeve may be provided with a stop element and a distal bone contacting surface. Reaming beyond the predetermined reaming depth forces the stop indicating sleeve proximally and urges the stop element on the sleeve into engagement with a stop engaging element provided on the reamer.

40 Claims, 4 Drawing Sheets

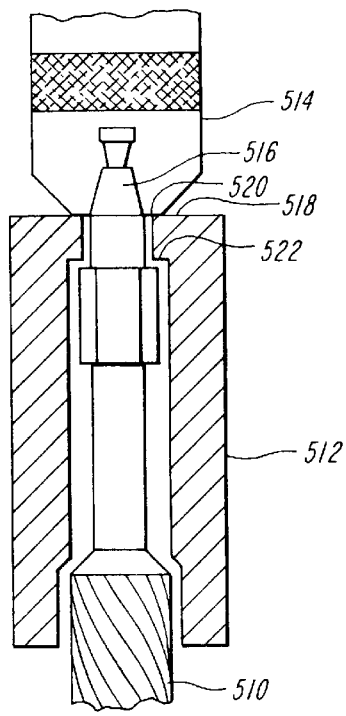
*FIG. 10*
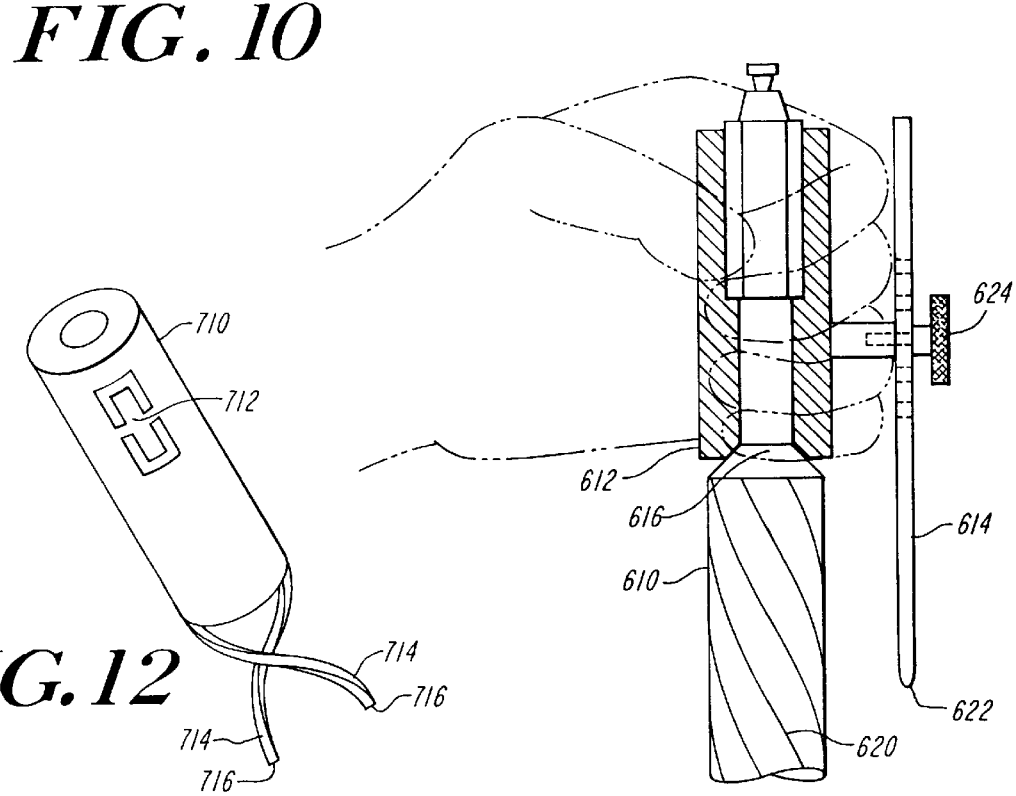
*FIG. 12*
*FIG. 11*

LONG BONE REAMER WITH DEPTH STOP INDICATOR

CROSS-REFERENCE TO RELATED APPLICATIONS

Not Applicable.

STATEMENT REGARDING FEDERALLY SPONSORED RESEARCH

Not Applicable.

FIELD OF THE INVENTION

The present invention relates to a instrument for reaming a long bone, in particular, a reaming instrument having a depth stop indicator.

BACKGROUND OF THE INVENTION

Orthopaedic surgeons must develop openings or cavities in long bones for a variety of reasons including fracture fixation and the implantation of stem based prostheses. Stems are used in prosthetic joint implants to anchor the prosthesis in a bone cavity. The bone receiving the stem is typically prepared by drilling a hole in the bone and creating an opening sized and contoured to receive the stem of the implant. The stem is inserted into a prepared cavity of a bone and a joint bearing surface attached or coupled to the stem, extends out to the cavity. An example of the preparation of a long bone for receipt of a femoral stem component of a total hip prosthesis is illustrated in U.S. Pat. No. 4,790,852 to Noiles which is hereby incorporated by reference.

When preparing a long bone for receipt of a stem, it is important to ream the bone to a suitable predetermined depth. Removal of more healthy bone than is necessary for implantation is always undesirable, and removal of too much or too little bone could result in an ill-fitted prosthesis. Orthopaedic surgeons use a variety of methods for indicating a predetermined reaming depth on a long bone reaming tool. Some surgeons simply mark the desired depth on the reamer with a pen so that the surgeon will know that the proper depth has been reached when the marking reaches the leading edge of the bone being reamed. This method has the disadvantage that markings can often be removed from the reamer by contact with body tissues or fluids during the reaming process.

Some orthopaedic instrumentation manufacturers have tried to improve depth markings on reamers by providing grooves transverse to the length of the reamer to provide a visual indicator to the surgeon similar to those made by pen. There are disadvantages to this approach as well. Transverse grooves may structurally weaken the reamer, shortening its useful life and possibly causing the reamer to fail during surgery. Additionally, the same reamer may be used to ream to a variety of different depths depending on the size of the stem being implanted. As a result, a large number of reamers each having a different depth marking must be maintained, resulting in an undesirable increase in instrument inventory. Alternatively, reamers must have multiple depth markings, which may result in confusion during reaming as to which is the correct depth mark.

Accordingly, it is an object of the present invention to provide a means for positively indicating a predetermined depth for a reamer while avoiding the aforementioned disadvantages.

SUMMARY OF THE INVENTION

The present invention provides an orthopaedic instrument system and method for reaming a long bone. The instrument system includes an elongate reamer having a proximal portion and a bone contacting surface with an integral cutting element. A stop indicating sleeve having an axial bore and a stop indicating element is removably disposed about the reamer. During reaming, when the reamer reaches a predetermined reaming depth, the stop indicating element indicates to the surgeon that the desired depth has been reached.

In one embodiment, the stop indicating sleeve is provided with a stop element and a distal bone contacting surface. When the distal bone contacting surface contacts a portion of the long bone not reamed by the reamer, continued reaming forces the stop indicating sleeve proximally and urges the stop element on the sleeve into engagement with a stop engaging element provided on the reamer. The stop member may be selectively movable between a first, disengaged position in which the stop member does not engage the stop engaging member on the reamer, and a second, engaged position wherein the stop member engages the stop engaging member to prevent proximal motion of the stop indicating sleeve relative to the reamer.

Alternatively, proximal motion of sleeve with respect to the reamer may itself be a stop indication, alerting the surgeon that the predetermined reaming depth has been reached. In another embodiment, the sleeve may include a visual stop indicating element having a diameter no greater than the diameter of the reamer. In one example, this embodiment may include at least one leg sized to fit within a flute in the reamer and having a length such that when the distal end of the leg has reached the edge of the long bone being reamed, the predetermined reaming depth has been reached.

BRIEF DESCRIPTION OF THE DRAWINGS

The invention will be more fully understood by reference to the following detailed description when considered in conjunction with the accompanying drawings, in which:

FIG. 10 illustrates an additional orthopaedic reaming system of the invention having a stop indicating sleeve that contacts a tool chuck;

FIG. 11 illustrates an additional orthopaedic reaming system of the invention including a stop indicating sleeve having an attached rod; and FIG. 12 illustrates a stop indicating sleeve useful with the invention having at least one stop indicating leg.

DETAILED DESCRIPTION OF THE INVENTION

Figure 1:
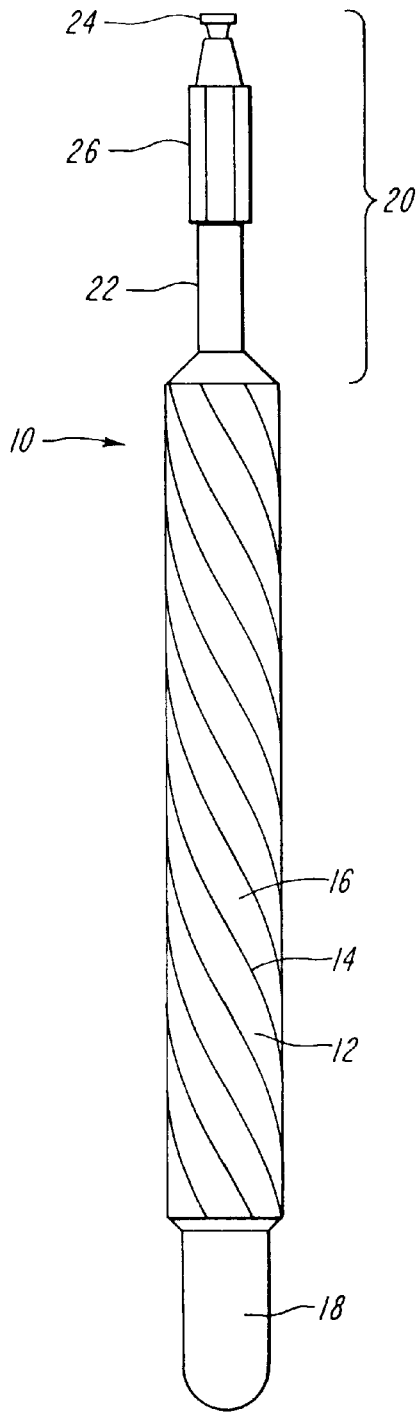
FIG. 1 illustrates a long straight reamer useful with the orthopaedic system of the invention.

A reamer 10 suitable for reaming a long bone and suitable for use with the orthopaedic instrument system of the invention is illustrated in FIG. 1. The reamer is generally cylindrical and elongate with a bone contacting surface 12 having one or more bone cutting edges 14. The illustrated reamer 10 has a plurality of flutes 16 arranged in a helical pattern with sharp edges 14 that are capable of cutting bone. Reamer 10 has a guide tip 18 on its distal end that may be used to guide the reamer 10 to a predrilled portion of the long bone. Reamer 10 is a straight reamer, though other reamer configurations may be used with the invention by a person of ordinary skill in the art.

Reamer 10 has a proximal portion 20 having a shaft 22 and tool mating elements on the shaft that may include a chuck engaging element 24 for cooperating with an instrument such as a power tool or drill to drive the reamer or a manual tool such as a T-handle, and a wrench engaging element 26 to allow a surgeon to drive the reamer 10 with a hand tool such as a wrench or socket.

Figure 2:
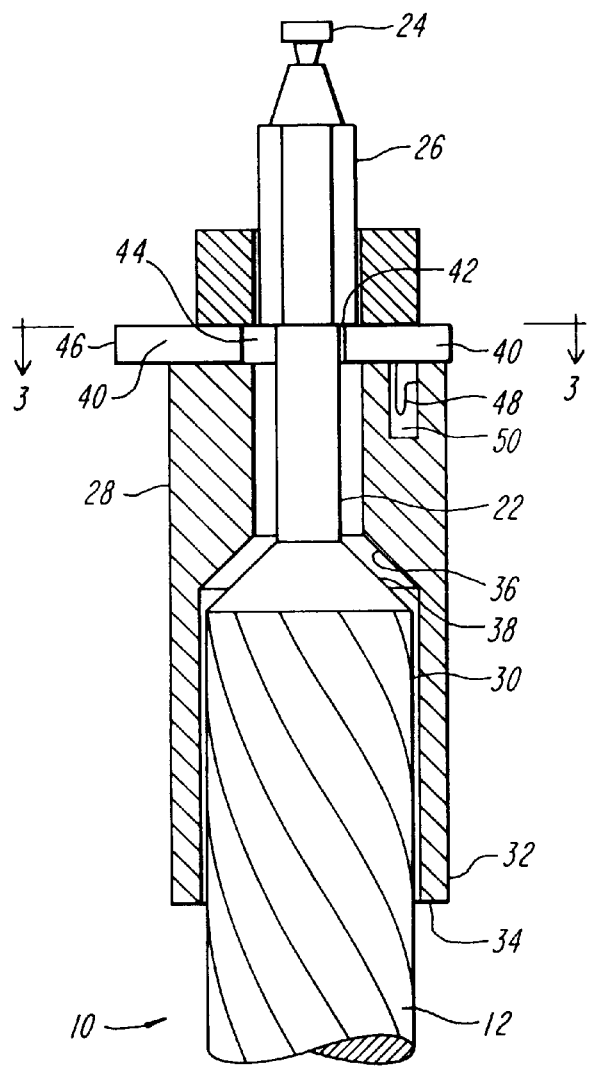
FIG. 2 illustrates, partly in section, an orthopaedic reaming system of the invention having a straight reamer and a stop indicating sleeve.

An orthopaedic instrument system of the invention including reamer 10 and a stop indicating sleeve 28 is shown in FIG. 2. Stop indicating sleeve 28 may be selected from a group of interchangeable sleeves having varying lengths, is generally cylindrical, and has axial bore 30 extending therethrough. The distal end 32 of the stop indicating sleeve 28 has a bone contacting distal surface 34. Reamer 10 fits within the axial bore 30 of the stop indicating sleeve 28 so that the distal end 32 of the sleeve extends around a portion of the bone contacting surface 12 of the reamer, while at least a portion of the proximal portion 20 of the reamer extends through the bore 30. Reamer 10 may fit within the axial bore 30 so that reamer 10 can rotate independently of the sleeve 28. This allows the surgeon to grasp the sleeve 28 during reaming if desired, and also avoids opportunities for a spinning sleeve to contact body tissue around the reaming area.

The axial bore 30 may include a ledge 36 that engages a feature on reamer 10, such as the proximal end 38 of the bone contacting surface 12, to prevent the stop indicating sleeve 28 from sliding distally off the reamer 10.

Figure 3A:
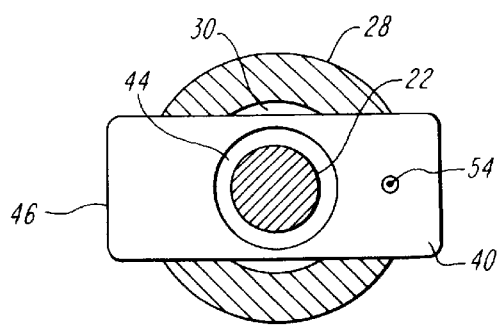
FIG. 3A is a cross sectional view of the orthopaedic reaming system of FIG. 2 taken along line 3—3 with a stop element in a first position.
Figure 3B:
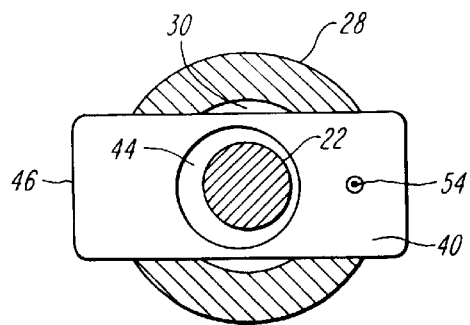
FIG. 3B is a cross sectional view of the orthopaedic reaming system of FIG. 2 taken along line 3—3 with the stop element in a second position.

The stop indicating sleeve 28 includes a stop element 40 that engages a stop engaging element 42 on reamer 10 to prevent the sleeve from sliding in a proximal direction relative to the reamer. As shown in FIGS. 2, 3A and 3B, stop element 40 is a biased sliding member with an aperture 44. Pressing on an extending portion 46 of the stop element 40 deforms bias member 48 and aligns the aperture 44 with at least a portion of the axial bore 30 of stop indicating sleeve 28 (FIG. 3A) and centers the aperture 44 with respect to the shaft 22 on the reamer 10. With the stop element 40 in this first position, the stop indicating sleeve 28 can slide over the proximal portion 20 of the reamer 10 and be fully disengaged from the reamer.

Releasing the stop element 40 and allowing the bias element 48 to return to its unbiased position causes the aperture 44 on the stop element 40 to become offset with respect to the reamer shaft 22 (FIG. 3B). In this second position, a proximal surface of stop element 40 adjacent to aperture 44 engages the stop engaging element 42 on the reamer 10. As shown in FIG. 2, the stop engaging element 42 may be the distal end of the wrench engaging element 26. A person of ordinary skill in the art will readily recognize that other stop engaging elements can be provided on the reamer 10 to engage the stop element 40 to prevent the stop indicating sleeve from sliding toward the proximal end 20 of reamer 10.

Figure 4:
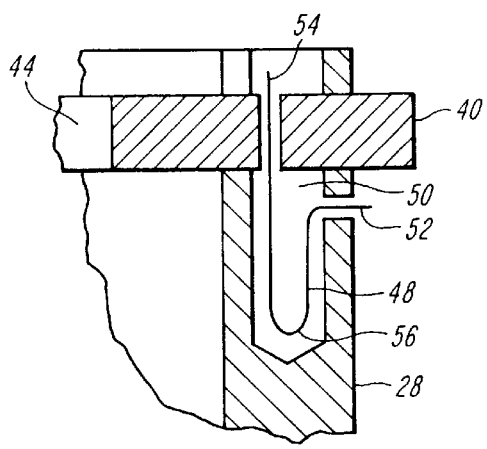
FIG. 4 illustrates a bias member used with the stop indicating sleeve of FIG. 2.

Bias element 48, illustrated in FIG. 4, is formed of a resilient material and can be located within a bore 50 in the body of stop indicating sleeve 28. The bias element 48 has a first end 52 that engages the body of the stop indicating sleeve 28, a second end 54 that engages the stop element 40, and at least one curve 56 provided between the first and second ends in a configuration that allows the bias element 48 to bias the sliding stop element 40 toward the second of the first and second positions illustrated in FIGS. 3A and 3B respectively.

The reamer and stop indicating sleeve of the invention may be used to ream any long bone. In particular, the instruments of the invention are useful for reaming long bones such as the femur, tibia or humerus for receipt of a stem based prosthesis. Reamer 10 may be made from any material useful for bone cutting applications and may, for example, be made of heat treated stainless steel. Reamer 10 generally varies in length from about 90 to 300 millimeters; for primary hip stem implantation into a femur, the length will vary from about 120 to 160 mm. Typically, the desired reaming depth will be equal to, or slightly longer than the length of the stem being implanted in the long bone.

An instrument set of the invention may include reamers of a single predetermined length, such as 260 or 300 mm, which would be long enough for even the longest of revision hip stems, and a variety of cutting diameters (generally 6 to 21 mm for most applications). Alternatively, a small number of different length reamers could be provided for different applications, e.g., a reamer length for hip revision surgery, a reamer length for primary hip surgery, a reamer length for tibial implant surgery, etc. A number of stop indicating sleeves can then be provided to adjust the effective reamer length to the desired value.

For example, to ream a femur to receive a hip stem having a length of 160 mm and a diameter of 19 mm given a set of 260 mm length reamers, a surgeon would choose the 19 mm diameter reamer 10, and a stop indicating sleeve 28 that would limit the effective reaming length to 160 mm. Such a stop indicating sleeve 28 would cover 100 mm of the reaming surface 12 of the reamer 10 when disposed on the reamer 10 so that the stop member 40 is in contact with the stop engaging element 42. The surgeon would then manually engage the stop element 40 by pressing on the extending portion 46 to align the aperture 44 with the axial bore 30 of the sleeve 28, and sliding the stop indicating sleeve 28 over the proximal end 20 of reamer 10.

Reamer 10 could then be employed, for example, to ream the medullary canal of the proximal femur of a patient. An example of such reaming using conventional instrumentation is illustrated in FIG. 4 of U.S. Pat. No. 4,790,852. In this example, following proximal femur resection, the surgeon may use reamer 10, having stop indicating sleeve 28 disposed thereon as described above, to ream the canal until the distal bone-contacting end 34 of the stop indicating sleeve 28 contacts the resected portion of the femur around the reamed hole. When the distal bone-contacting end 34 contacts the femur, the stop indicating sleeve 28 is forced toward the proximal end 20 of reamer 10, and the stop element 40 engages the stop engaging element 42 on the reamer 10 to prevent further proximal motion. The stop indicating sleeve 28 thus positively prevents reamer 10 from moving any deeper into the femur.

Figure 5:
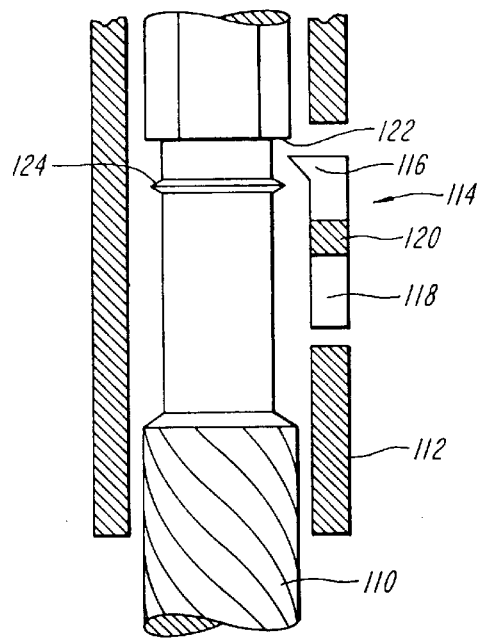
FIG. 5 illustrates an additional orthopaedic reaming system of the invention having a stop indicating sleeve with a biased lever member.
Figure 6:
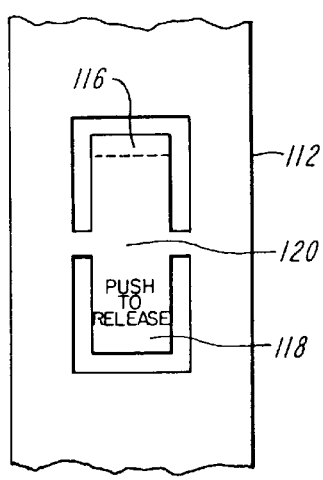
FIG. 6 is a side view of the biased lever member used in the system of FIG. 5.

Another orthopaedic instrument system of the invention, illustrated in FIGS. 5 and 6, includes reamer 110 and stop indicating sleeve 112. Sleeve 112 has a biased lever element 114 including a stop element 116, a release element 118, and a sleeve connecting element 120. Biased lever element 114 is resiliently connected to sleeve 112 and is biased to a stop engaging position wherein stop element 116 engages a stop engaging element 122 on reamer 110 to prevent motion in a proximal direction. The stop engaging position is released by pressing on the release element 118 of the biased lever 114 to disengage stop element 116 from stop engaging element 122. A circumferential protrusion 124, or a plurality of such protrusions, may also be provided on reamer 110 to engage stop element 116 to prevent sleeve 112 from sliding distally with respect to reamer 110.

Figure 7:
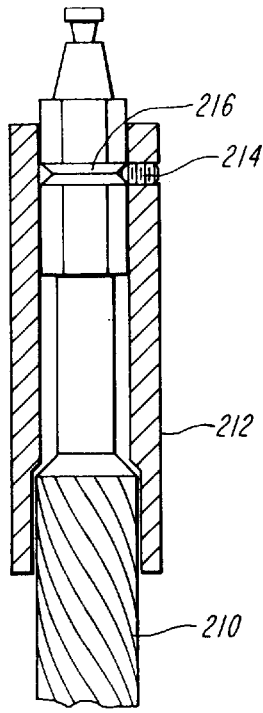
FIG. 7 illustrates an additional orthopaedic reaming system of the invention having a stop indicating sleeve with a detent member.

An additional orthopaedic reaming system of the invention having reamer 210 and stop indicating sleeve 212 is shown in FIG. 7. Sleeve 212 includes a detent member 214 which may be a set screw, a biased detent member such as a spring ball, or another detent member that may be selected by a person of ordinary skill in the art. As shown, detent member 214 engages a groove 216 as a stop engaging member on reamer 210, however, detent member 214 may engage other features of the reamer to prevent distal motion of sleeve 212 as well.

Figure 8:
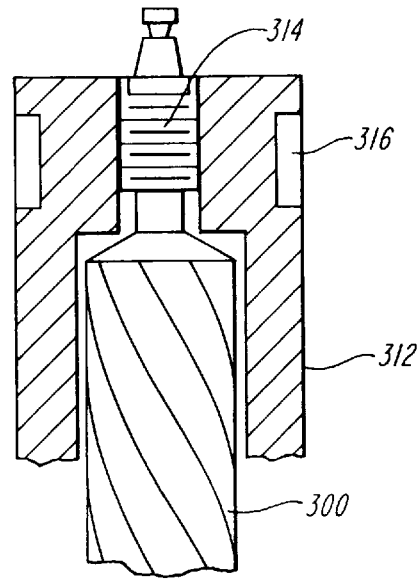
FIG. 8 illustrates an additional orthopaedic reaming system of the invention having a stop indicating sleeve in threaded engagement with a reamer.

FIG. 8 illustrates an orthopaedic reaming system of the invention having a reamer 310 threadedly engaged with a stop indicating sleeve 312. In this configuration, the threading 314 on the reamer 310 and sleeve 312 will be in the opposite direction of the rotation of the reamer for the purpose of reaming bone. That is, if a right-hand rotation is used to cut bone, threads 314 will be left-handed. Wrench engaging features 316 may also be provided on sleeve 312 to facilitate the threaded engagement with the reamer 310.

Figure 9:
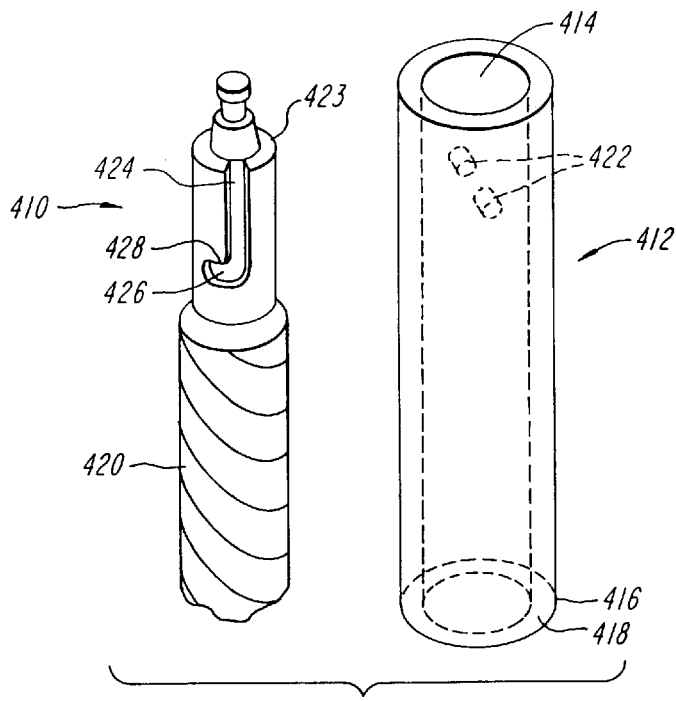
FIG. 9 illustrates an additional orthopaedic reaming system of the invention including a stop indicating sleeve having a slot and pin engagement with a reamer.

An additional reamer 410 and stop indicating sleeve 412 of the orthopaedic reaming system of the invention are illustrated in FIG. 9. Sleeve 412 is generally cylindrical with an axial bore 414 and a distal end 416 having a bond contacting surface 418. The axial bore 414 is sized so that the distal portion of the sleeve 412 fits over the bone contacting surface 420 of reamer 410. Sleeve 412 further includes a stop element in the form of two pins 422 formed within axial bore 414. Of course, a person of ordinary skill in the art may use more or fewer stop elements as the circumstances of a particular instrument require. Longitudinal slots 424 (one shown) slidingly receive pins 422 to allow the sleeve 412 to slide over the proximal portion 423 of reamer 410. A transverse slot 426, preferably extending in a direction opposite to the direction of rotation of reamer 410, communicates with the distal end of longitudinal slot 424. After sliding sleeve 412 over the proximal portion 423 of reamer 410, twisting the sleeve 412 with respect to reamer 410 fully engages pins 422 with transverse slots 426. When so engaged, the proximal wall 428 of slot 426 becomes a stop engaging element for pins 422 and prevents reamer 410 from being deployed more deeply than desired in a patient's long bone.

As shown in FIG. 10, an orthopaedic reaming instrument of the invention may have reamer 510, sleeve 512 and chuck 514 engaged to the proximal end 516 of the reamer. In this configuration, the proximal portion 518 of sleeve 512 abuts the distal portion 520 of chuck 514 to prevent proximal movement of the sleeve with respect to reamer 510 and chuck 514 acts as a stop engaging element. In addition, step 522 may be provided on the sleeve to engage a feature of reamer 510 to prevent distal movement of the sleeve with respect to the reamer. In this way, a rigid connection between reamer 510, sleeve 512 and chuck 514 may be achieved.

Reaming systems of the invention may also provide visual stop indications in addition to or in place of physical stop indications. For example, using reamer 10 and stop indicating sleeve 28 (FIG. 2), when ledge 36 on the sleeve rests on the proximal end 38 of the bone contacting surface 12 of reamer 10, a gap exists between stop element 40 and stop engaging element 42. During reaming, the distal bone contacting surface 34 of sleeve 28 will contact the bone being reamed and this contact moves sleeve 28 proximally with respect to the reamer 10 until stop element 40 and stop engaging element 42 make contact. This relative movement provides a visual indication to the surgeon that the physical stop is about to be reached. Further, sleeve 28 could be configured without stop element 40. Such a sleeve could readily be configured to provide a visual indication at the predetermined reaming depth rather than shortly before the predetermined reaming depth.

An additional orthopaedic reaming system of the invention using a visual stop indication, illustrated in FIG. 11, includes reamer 610, sleeve 612, and rod 614. Sleeve 612 slides over the proximal end 616 of reamer 610 and abuts the proximal edge 618 of the bone contacting surface 620 of reamer 610 to prevent the sleeve from sliding in a distal direction. A surgeon may hold the sleeve 612 in contact with a proximal edge 618 by holding the sleeve 612 and applying a slight distal pressure.

Rod 614 has a distal, bone contacting end 622 so that when reaming has reached the desired depth, the distal, bone contacting end 622 of rod 614 contacts unreamed bone and causes sleeve 612 to slide proximally with respect to reamer 610 giving the surgeon a visual indication that the desired depth has been reached. Rod 614 may be slidably attached to sleeve 614, for example, using thumb screw 624, so that the rod 614 may be adjusted for different desired reaming depths. Rod 614 may also have calibrated markings to allow more efficient adjustments to the desired reaming depth.

An additional stop indicating sleeve 710 having a visual stop indication is shown in FIG. 12. Sleeve 710 includes a biased lever element 712, similar in structure and operation to biased lever element 114 (FIGS. 5 and 6), and at least one leg 714 configured to fit within a reamer flute so that the reamer assembly, including sleeve 710, has a diameter that is no greater than the diameter of the reamed hole. This configuration is advantageous where the bone being reamed does not have a clear bone surface around the desired reaming position. The legs 714 are sized to fit within reamer flutes and indicate that the desired reaming depth has been reached when the distal ends 716 of legs 714 reach the edge of the bore being reamed.

It will be understood that the foregoing is only illustrative of the principles of the invention, and that various modifications of the disclosed orthopaedic reaming system, including combining features of the various disclosed embodiments, can be made by those skilled in the art without departing from the scope and spirit of the invention. All references cited herein are expressly incorporated by reference in their entirety.

What is claimed is:

1. An orthopedic instrument system for reaming a long bone comprising:

a fixed length elongate reamer having a proximal portion, a bone contacting outer surface, at least one bone cutting element integral with the bone contacting outer surface, and a single stop engaging element disposed thereon; and a stop indicating sleeve comprising a substantially cylindrical sleeve defining an axial bore, the sleeve being removably disposed about the elongate reamer and having a bone contacting distal end and a stop element, the stop element being selectively movable between a first, disengaged position in which the stop element does not engage the stop engaging element on the reamer, and a second, engaged position wherein the stop element engages the stop engaging element to prevent proximal motion of the stop indicating sleeve relative to the reamer;

wherein the stop element is biased to the second, engaged position; and wherein, at a predetermined reaming depth, the bone contacting distal end of the sleeve contacts a portion of the long bone not reamed by the elongate reamer and the stop element on the sleeve engages the stop engaging element disposed on the reamer to prevent the reamer from reaming the long bone further than the predetermined reaming depth.

2. The orthopaedic instrument system of claim 1, wherein the stop element comprises a sliding member.

3. The orthopaedic instrument system of claim 2, wherein the stop element includes an aperture that is at least partially aligned with the axial bore of the stop indicating sleeve.

4. The orthopaedic instrument system of claim 3, wherein a surface of the stop element adjacent the aperture contacts the stop engaging element when the stop element is in its second position.

5. The orthopaedic instrument system of claim 1, wherein the stop engaging element is integral with the proximal portion of the reamer.

6. The orthopaedic instrument system of claim 1, wherein the stop engaging element is provided on a power tool connecting element engaged with the proximal portion of the reamer.

7. The orthopaedic instrument system of claim 1, wherein the stop element comprises a biased lever.

8. The orthopaedic instrument system of claim 1, wherein the stop element comprises a detent element.

9. The orthopaedic instrument system of claim 8, wherein the detent element is biased to the second, engaged position.

10. The orthopaedic instrument system of claim 9, wherein the detent element is a spring ball.

11. The orthopaedic instrument system of claim 8, wherein the detent element is a set screw.

12. The orthopaedic instrument system of claim 1, wherein the stop indicating sleeve is in a threaded engagement with the reamer.

13. The orthopaedic instrument system of claim 1, wherein the bone contacting distal end of the stop indicating sleeve is provided on an attached rod.

14. The orthopaedic instrument system of claim 13, wherein the attached rod is adjustable to change the effective reaming depth of the system.

15. An orthopedic instrument system for reaming a long bone comprising:

an elongate reamer having a proximal portion, a bone contacting outer surface, at least one bone cutting element integral with the bone contacting outer surface, and a stop engaging element disposed thereon; and a stop indicating sleeve comprising a substantially cylindrical sleeve defining an axial bore, the sleeve being removably disposed about the elongate reamer and having a bone contacting distal end and a stop element;

wherein, at a predetermined reaming depth, the bone contacting distal end of the sleeve contacts a portion of the long bone not reamed by the elongate reamer and the stop element on the sleeve engages the stop engaging element disposed on the reamer to prevent the reamer from reaming the long bone further than the predetermined reaming depth;

wherein the stop indicating sleeve includes at least one pin engageable within at least one slot provided on the proximal portion of the reamer; and wherein the at least one slot provided on the proximal portion of the reamer has a longitudinal portion and a transverse portion.

16. The orthopaedic instrument system of claim 15, wherein the transverse portion is oriented in a direction opposite to a direction of reaming rotation of the reamer.

17. An orthopedic instrument kit for reaming a long bone comprising:

a fixed length elongate reamer having a proximal portion, a bone contacting outer surface, and at least one bone cutting element integral with the bone contacting outer surface; and a plurality of fixed length interchangeable stop indicating sleeves engageable with the reamer, each sleeve having a different length and comprising a substantially cylindrical sleeve defining an axial bore removably disposed about the elongate reamer and a stop indicating element;

wherein, for a stop indicating sleeve selected from the plurality of stop indicating sleeves for reaming to a predetermined reaming depth engaged with the fixed length reamer, the stop indicating element indicates that the reamer has reached the predetermined depth.

18. The orthopaedic reaming system of claim 17, wherein the stop indicating element includes a distal bone contacting end that causes relative motion between the stop indicating sleeve and reamer upon contact with an unreamed surface of the long bone.

19. The orthopaedic reaming system of claim 18, wherein when the distal bone contacting end contacts an unreamed surface of the long bone, a stop element provided on the stop indicating sleeve engages a stop engaging element on the reamer to provide a physical stop indication.

20. The orthopaedic reaming system of claim 18, wherein the distal bone contacting surface is provided on a rod attached to the stop indicating sleeve that is adjustable to effect the predetermined reaming depth of the system.

21. The orthopaedic reaming system of claim 17, wherein the stop indicating element is a visual stop indicating element that has a diameter no larger than a diameter of a bone contacting portion of the reamer.

22. The orthopaedic reaming system of claim 21, wherein the stop indicating element comprises at least one leg member sized to fit within a flute on the reamer.

23. A method for reaming a long bone to a predetermined depth comprising the steps of:

providing an elongate reamer having a proximal portion, a bone contacting outer surface, at least one bone cutting element integral with the bone contacting outer surface;

providing a plurality of fixed length interchangeable stop indicating sleeves, each sleeve having a different length, comprising a substantially cylindrical sleeve defining an axial bore removably disposed about the elongate reamer and a stop indicating element;

selecting a stop indicating sleeve having a desired length corresponding to a predetermined reaming depth for the reamer;

engaging a long bone with the reamer to create a bore within the bone of increasing depth wherein, at a predetermined reaming depth, the stop indicating element indicates that the predetermined depth has been reached; and ceasing increasing the depth of the reamed bore and disengaging the reamer from the long bone.

24. The reaming method of claim 23, wherein the stop indicating element includes a distal bone contacting end that causes relative motion between the stop indicating sleeve and reamer upon contact with an unreamed surface of the long bone.

25. The reaming method of claim 24, wherein when the distal bone contacting end contacts an unreamed surface of the long bone, a stop element provided on the stop indicating sleeve engages a stop engaging element on the reamer to provide a physical stop indication.

26. The orthopaedic reaming system of claim 23, wherein the stop indicating element is a visual stop indicating element that has a diameter no larger than a diameter of a bone contacting portion of the reamer.

27. The orthopaedic reaming system of claim 26, wherein the stop indicating element comprises at least one leg member sized to fit within a flute on the reamer.

28. The orthopedic instrument kit of claim 20, wherein the stop indicating element comprises a stop element selectively movable between a first, disengaged position in which the stop element does not engage a stop engaging element on the reamer, and a second, engaged position wherein the stop element engages the stop engaging element to prevent proximal motion of the stop indicating sleeve relative to the reamer.

29. The orthopedic instrument kit of claim 28, wherein the stop element is biased to the second, engaged position.

30. The orthopaedic instrument kit of claim 28, wherein the stop element comprises a sliding member.

31. The orthopaedic instrument kit of claim 30, wherein the stop element includes an aperture that is at least partially aligned with the axial bore of the stop indicating sleeve.

32. The orthopaedic instrument kit of claim 31, wherein a surface of the stop element adjacent the aperture contacts the stop engaging element when the stop element is in its second position.

33. The orthopaedic instrument kit of claim 28, wherein the stop engaging element is integral with the proximal portion of the reamer.

34. The orthopaedic instrument kit of claim 28, wherein the stop engaging element is provided on a power tool connecting element engaged with the proximal portion of the reamer.

35. The orthopaedic instrument kit of claim 28, wherein the stop element comprises a biased lever.

36. The orthopaedic instrument kit of claim 28, wherein the stop element comprises a detent element.

37. The orthopaedic instrument kit of claim 36, wherein the detent element is biased to the second, engaged position.

38. The orthopaedic instrument kit of claim 37, wherein the detent element is a spring ball.

39. The orthopaedic instrument kit of claim 36, wherein the detent element is a set screw.

40. The orthopaedic instrument kit of claim 17, wherein the stop indicating sleeve is in a threaded engagement with the reamer.

* * * * *